(12) United States Patent
Oostman, Jr. et al.

(10) Patent No.: US 8,152,827 B2
(45) Date of Patent: Apr. 10, 2012

(54) SYSTEMS AND METHODS FOR HARVESTING, STORING, AND IMPLANTING HAIR GRAFTS

(75) Inventors: Clifford A. Oostman, Jr., Hansville, WA (US); Tomás Meléndez, San Jose, CA (US)

(73) Assignee: Restoration Robotics, Inc., Mountain View, CA (US)

( * ) Notice: Subject to any disclaimer, the term of this patent is extended or adjusted under 35 U.S.C. 154(b) by 588 days.

(21) Appl. No.: 12/348,811

(22) Filed: Jan. 5, 2009

(65) Prior Publication Data

US 2009/0178943 A1    Jul. 16, 2009

Related U.S. Application Data

(60) Provisional application No. 61/020,572, filed on Jan. 11, 2008.

(51) Int. Cl.
*A61B 17/34* (2006.01)
(52) U.S. Cl. ...................................................... 606/187
(58) Field of Classification Search ............... 606/9, 36, 606/130, 131, 133, 181–184, 185, 187; 220/507, 220/500, 23.83, 556, 555; 206/372, 349; D9/760, 759, 756, 737; 600/574–584
See application file for complete search history.

(56) References Cited

U.S. PATENT DOCUMENTS

| | | |
|---|---|---|
| 2,366,886 A | 1/1945 | Tuyl |
| 4,154,239 A | 5/1979 | Turley |
| 4,451,254 A | 5/1984 | Dinius et al. |
| 4,485,933 A | 12/1984 | Sykes |
| 5,071,346 A * | 12/1991 | Domaas .......................... 433/77 |

(Continued)

FOREIGN PATENT DOCUMENTS

WO    WO 95/28896    11/1995

(Continued)

OTHER PUBLICATIONS

Communication from Australian Patent Office, mailed Apr. 1, 2011, in relation to commonly assigned Australian Patent Application No. 12008307698, which is an Australian National Stage filing of PCT/US2008/010034. Applicant Restoration Robotics, Inc. (4 pages).

(Continued)

*Primary Examiner* — Ryan Severson
*Assistant Examiner* — Katherine M Shi
(74) *Attorney, Agent, or Firm* — Lena I. Vinitskaya; Guy Cumberbatch

(57) ABSTRACT

A system and method for harvesting, storing, and implanting biological unit delivery tools, particularly useful to facilitate robotic hair transplant procedures. A storage device includes a lower module having a plurality of receptacles for containing delivery tools, for example small tubular follicular unit implant needles. The receptacles may contain liquid for maintaining hydration of the biological unit. The lower module may be manipulated by an automated system which includes a pick and placed collet that handles the delivery tools one at a time in an implant procedure. An upper module registers with the lower module and provides guide bores leading to the delivery tools in the receptacles. A biological unit removal tool, such as a follicular unit harvesting needle, can be carried by the collet and used to deposit biological units through the guide bores and into each delivery tool. Each receptacle may include means for retaining the delivery tool therein to help the collet cleanly insert and release the tool.

15 Claims, 6 Drawing Sheets

U.S. PATENT DOCUMENTS

| | | | |
|---|---|---|---|
| 5,417,683 A | | 5/1995 | Shiao |
| 5,439,475 A | * | 8/1995 | Bennett ............... 606/187 |
| 5,584,851 A | | 12/1996 | Banuchi |
| 5,611,811 A | | 3/1997 | Goldberg |
| 5,643,308 A | | 7/1997 | Markman |
| 5,690,223 A | * | 11/1997 | Wood .................. 206/363 |
| 5,782,843 A | | 7/1998 | Aasberg |
| 5,782,851 A | | 7/1998 | Rassman |
| 5,792,169 A | | 8/1998 | Markman |
| 5,817,120 A | * | 10/1998 | Rassman ............... 606/187 |
| 5,827,297 A | | 10/1998 | Boudjema |
| 5,868,758 A | | 2/1999 | Markman |
| 5,873,888 A | | 2/1999 | Costanzo |
| 5,895,403 A | | 4/1999 | Collinsworth |
| 5,951,572 A | | 9/1999 | Markman |
| 6,027,512 A | | 2/2000 | Bridges |
| 6,056,736 A | | 5/2000 | Markman |
| 6,059,807 A | | 5/2000 | Boudjema |
| 6,270,511 B1 | | 8/2001 | Markman |
| 6,572,625 B1 | * | 6/2003 | Rassman ............... 606/133 |
| 6,585,746 B2 | | 7/2003 | Gildenberg |
| 6,973,931 B1 | | 12/2005 | King |
| 7,144,406 B2 | | 12/2006 | Pak et al. |
| 7,481,820 B1 | | 1/2009 | Keene |
| 7,627,157 B2 | | 12/2009 | Qureshi et al. |
| 2002/0103222 A1 | | 8/2002 | Mangat |
| 2003/0040766 A1 | | 2/2003 | Werner |
| 2003/0087454 A1 | | 5/2003 | Schultz et al. |
| 2004/0116942 A1 | | 6/2004 | Feller |
| 2004/0220589 A1 | | 11/2004 | Feller |
| 2006/0127881 A1 | | 6/2006 | Wong et al. |
| 2006/0195047 A1 | * | 8/2006 | Freeman et al. ......... 600/583 |
| 2007/0078466 A1 | | 4/2007 | Bodduluri |
| 2007/0287984 A1 | | 12/2007 | Lobl et al. |
| 2008/0033455 A1 | | 2/2008 | Rassman et al. |
| 2008/0050805 A1 | | 2/2008 | Cole et al. |
| 2009/0052738 A1 | | 2/2009 | Qureshi et al. |
| 2009/0087830 A1 | | 4/2009 | Oostman |
| 2009/0088720 A1 | | 4/2009 | Oostman |

FOREIGN PATENT DOCUMENTS

| | | |
|---|---|---|
| WO | 01/64111 | 9/2001 |
| WO | 2005/009491 | 2/2005 |
| WO | 2007/021904 | 2/2007 |
| WO | WO 2007/021904 | 2/2007 |
| WO | 2007/041267 | 4/2007 |
| WO | 2008/024954 A2 | 2/2008 |
| WO | 2008/024955 A2 | 2/2008 |

OTHER PUBLICATIONS

Final Office Action mailed Mar. 10, 2011, in connection with U.S. Appl. No. 12/196,524 (13 pages).

Response to Final Office Action mailed Mar. 10, 2011, in connection with U.S. Appl. No. 12/196,524 (12 pages).

Dong-Youn Lee, Joo-Heung Lee, Jun-Mo Yang, Eil-Soo Lee. "New Instrument for Hair Transplant: Multichannel Hair Transplanter", Dermatol Surg 2005, 31: 379. Published by BC Decker Inc.

William R. Rassman, MD; Robert M. Bernstein, MD. "Rapid Fire Hair Implanter Carousel". Dermatologic Surgery, vol. 24, 1998, pp. 623-627.

PCT International Search Report and Written Opinion of PCT/US2008/010034, Applicant Restoration Robotics, Inc. Forms PCT/ISA/210, 220 and 237, dated Feb. 4, 1009 (16 pages).

PCT International Search Report and Written Opinion of PCT/US2009/030326, Applicant Restoration Robotics, Inc. (Agent's File Reference: RR-015PCT) Forms PCT/ISA/210, 220 and 237, dated May 14, 1009 (15 pages).

Robert M. Bernstein, MD and William R. Rassman, MD. "The Logic of Follicular Unit Transplantation". Dermatologic Clinics vol. 17, No. 2, Apr. 1999. pp. 277-296.

Non-Final Office Action Mailed Apr. 13, 2010, in relation to U.S. Appl. No. 12/196,524, Applicant Restoration Robotics, Inc., (14 pages).

Response to Office Action submitted Jun. 14, 2010, in relation to U.S. Appl. No. 12/196,524, Applicant Restoration Robotics, Inc., (9 pages).

Interview Summary Mailed Jun. 21, 2010, in relation to U.S. Appl. No. 12/196,524, Applicant Restoration Robotics, Inc., (4 pages).

Non-Final Office Action Mailed Mar. 3, 2011, in relation to U.S. Appl. No. 12/194,370, Applicant Restoration Robotics, Inc., (14 pages).

Non-Final Office Action Mailed Oct. 7, 2010, in relation to U.S. Appl. No. 12/196,524, Applicant Restoration Robotics, Inc., (12 pages).

Response to Non-Final Office Action Mailed Oct. 7, 2010, in relation to U.S. Appl. No. 12/196,524, Applicant Restoration Robotics, Inc., (11 pages).

Office Action mailed Nov. 9, 2011, in relation to commonly assigned U.S. Appl. No. 12/194,370 (15 pages).

* cited by examiner

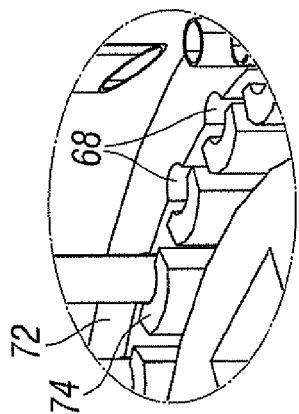
Fig. 2C
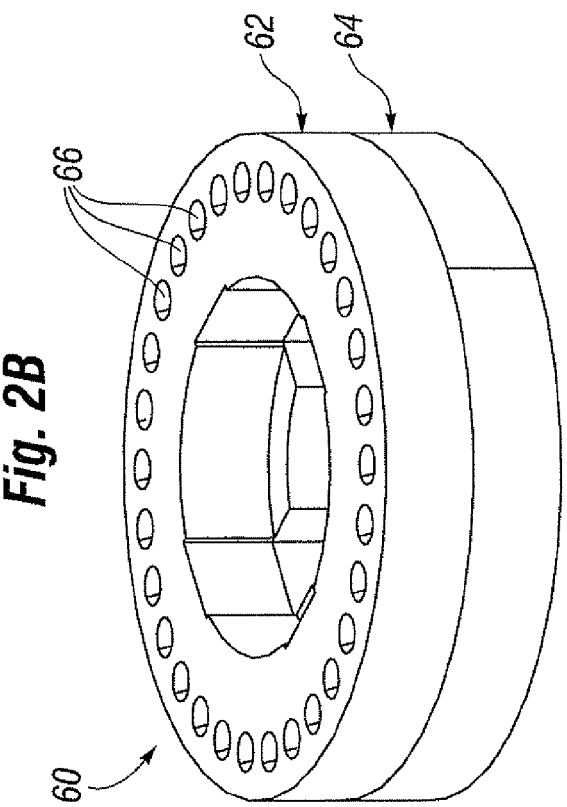
Fig. 2B
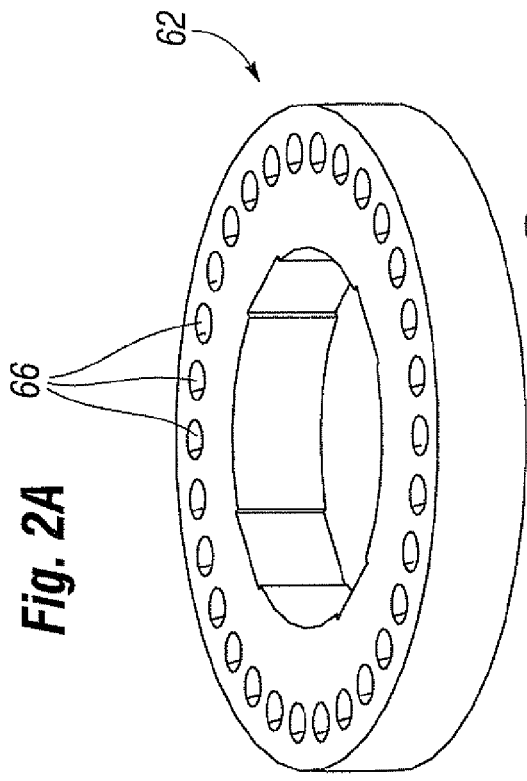
Fig. 2A
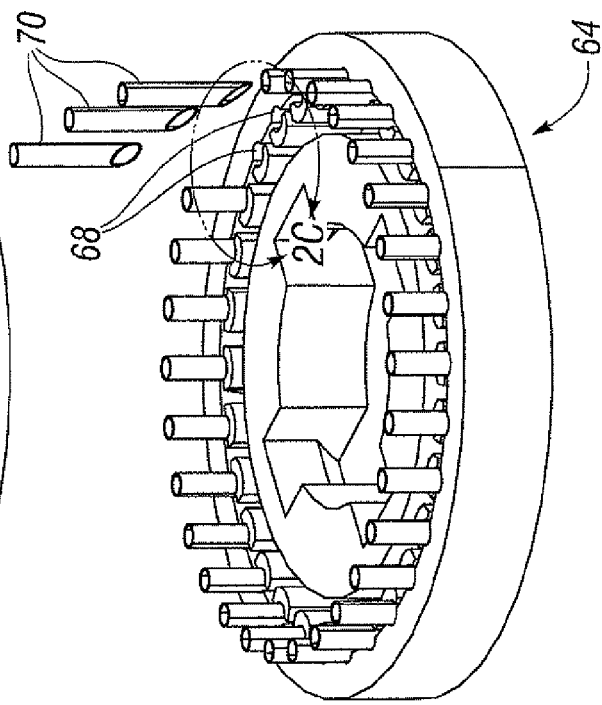

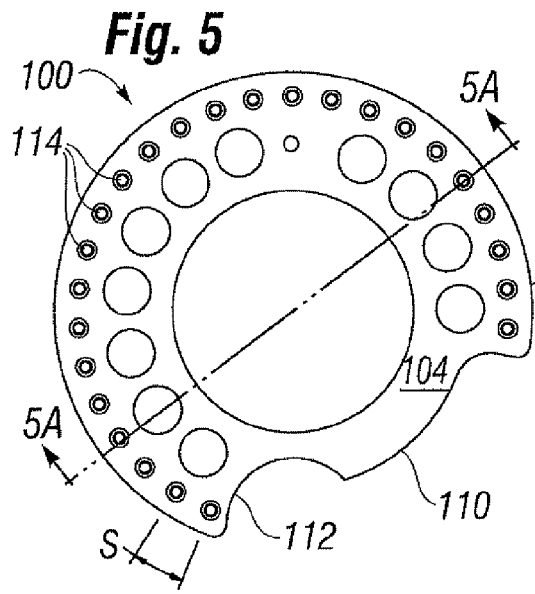
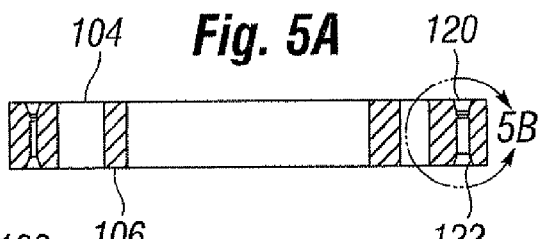
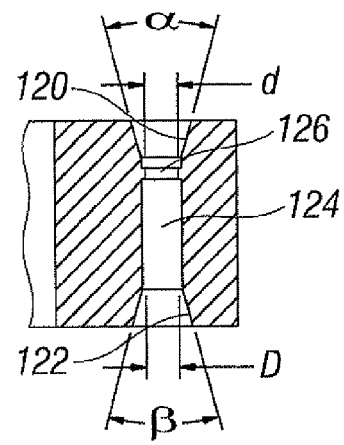
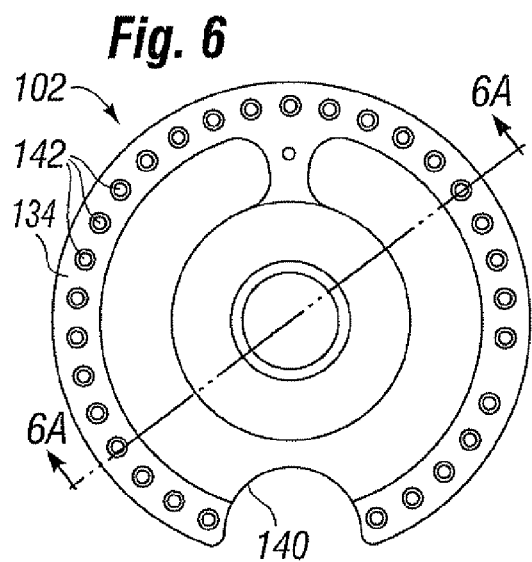
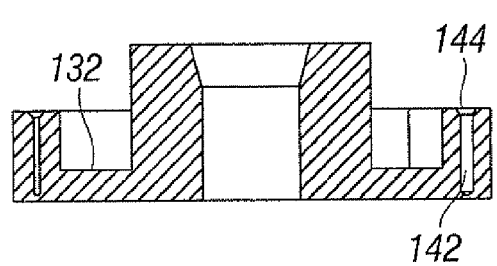
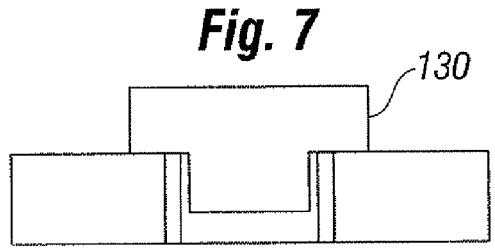

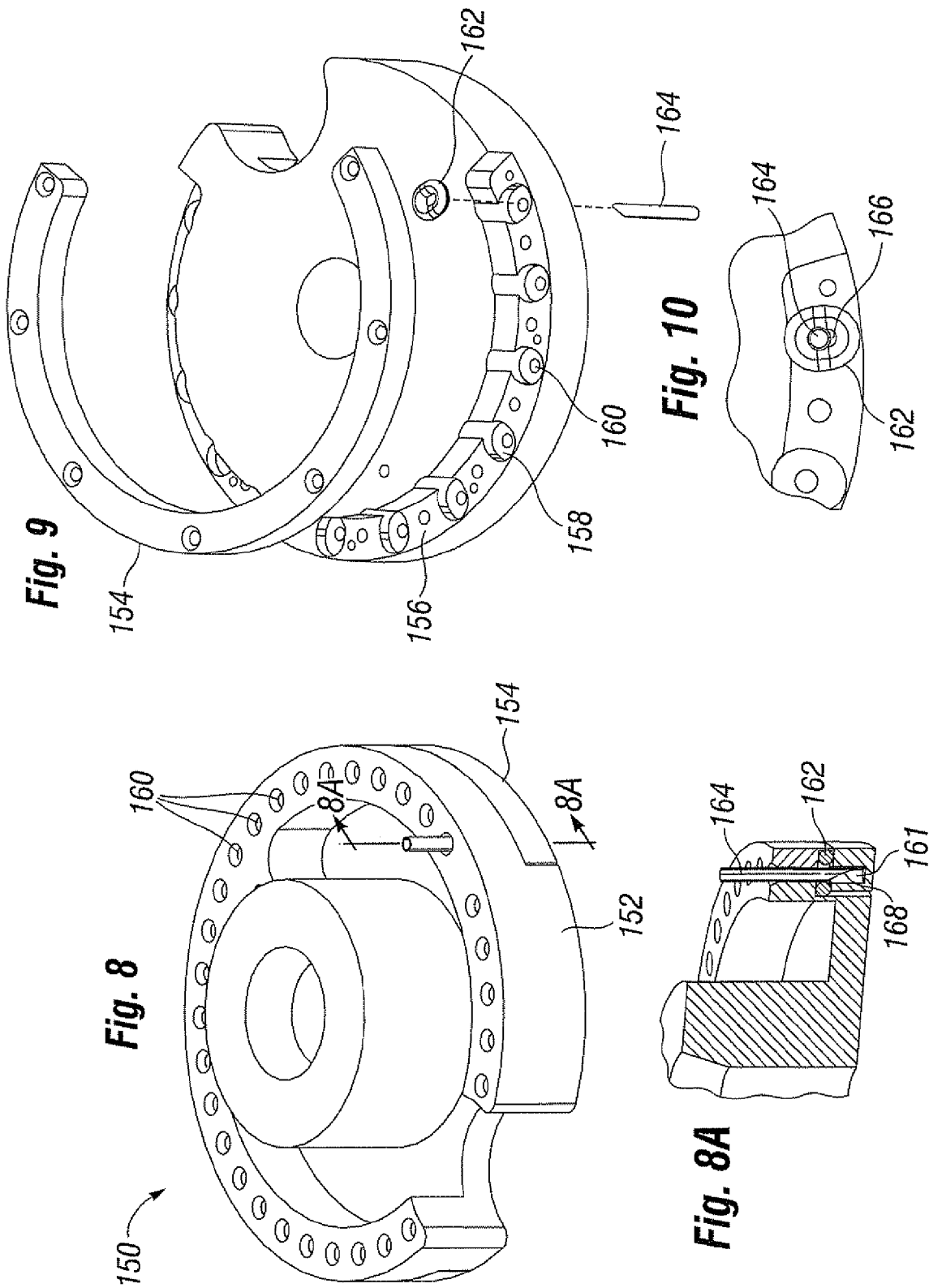

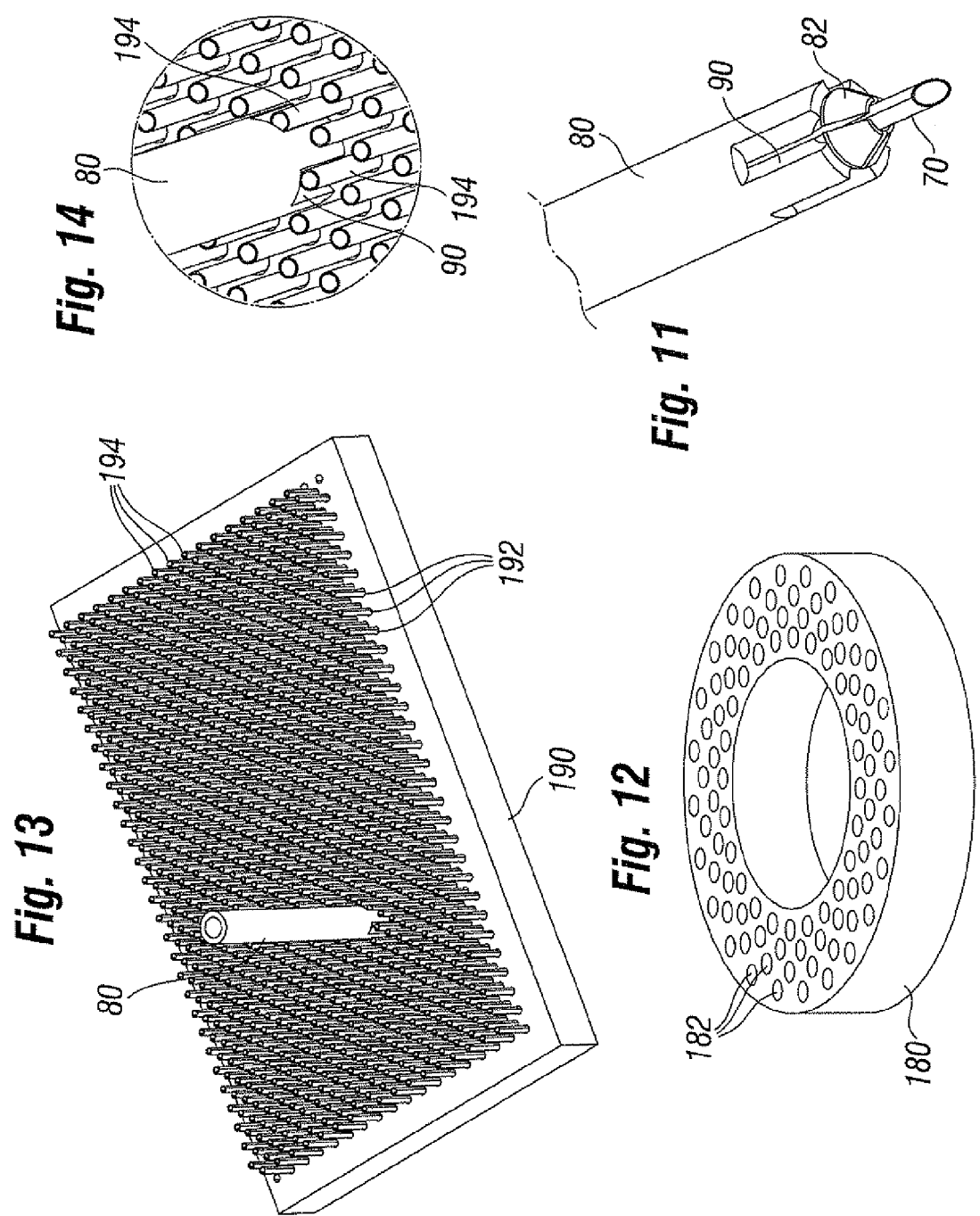

SYSTEMS AND METHODS FOR HARVESTING, STORING, AND IMPLANTING HAIR GRAFTS

CROSS REFERENCE TO RELATED APPLICATIONS

The present application claims priority to U.S. Provisional Patent Application No. 61/020,572, filed on Jan. 11, 2008, the disclosure of which is incorporated by reference herein in its entirety.

FIELD OF THE INVENTION

The present invention relates generally to devices, systems and methods for storing objects used in cosmetic and dermatological procedures, and it is especially useful for storing hair grafts or hair follicles.

BACKGROUND OF THE INVENTION

Various cosmetic and dermatological procedures exist where there is a need to collect and store biological units, for example, for future examination, or processing, or reuse. Hair transplantation procedures are among those well-known procedures, and typically involve harvesting donor hair grafts from the donor areas of the patient's body, most commonly scalp, and implanting them in a bald area (recipient area).

Various procedures for hair transplantation have been previously disclosed, including both manual and mechanized to certain degrees of automation. In one well-known manual process, a linear portion of the scalp is removed from a donor area by dissection with a scalpel down into the fatty subcutaneous tissue. The strip is dissected (under a microscope) into the component follicular units, which are then implanted into a recipient area in respective puncture holes made by a needle. Forceps are typically used to grasp and place the follicular unit grafts into the needle puncture locations, although other instruments and methods are known for doing so.

During manual, semi-automatic, or robotically-assisted procedures for hair transplantation, it is usually desirable to collect and retain harvested follicular units or grafts in some storage device prior to their implantation. Similarly, in other cosmetic and dermatological procedures that require removal of the biological objects or tissue, it may be desirable to collect and store such objects before they are processed, reused or re-implanted. Often these storage devices consist of a container for bulk hair grafts, from which a technician plucks individual grafts for implant. While attempts were made to design some storage devices or cartridges for containing hair follicles for use in manual hair transplantation procedures, there is a need for an improved storage device with an improved design and which could be used in manual, partially or fully automated, or robotically-assisted systems and procedures.

SUMMARY OF THE INVENTION

In accordance with a general aspect of one of the inventions disclosed herein, a storage device for holding biological units includes a body defining a plurality of receptacles therein for holding delivery tools that carry biological units. A plurality of the delivery tools are stored in this manner in the storage device and selectively accessed to deliver the biological units to a target location. The process may be automated.

In accordance with one embodiment, the storage device holds a plurality of follicular unit delivery tools, and comprises upper and lower modules. The lower module defines a plurality of receptacles for receiving follicular unit delivery tools, each receptacle having an upper opening and a cross-sectional dimension suitable for closely containing a follicular unit delivery tool. The upper module is configured to register over the lower module and has a plurality of guide bores for the receptacles in the lower module. The guide bores align with corresponding receptacles when the upper module registers with the lower module. The follicular unit delivery tools may comprise, for example, follicular unit implant tools, or follicular unit harvest tools. The lower module of the storage device may be closed off at its lower end, and one or more of the plurality of receptacles of the lower module is configured to retain and/or to transport, for example, a liquid or gas to keep the follicular units/delivery tools moist. In some embodiments, one or more of the plurality of receptacles is interconnected and configured to retain and/or transport liquid or gas. Both the lower module and upper module may have various shapes, for example, annular, disc or partial disc shapes, or both may be rectilinear. In one version, the lower module comprises a central upstanding hub having an outer diameter, and the upper module has a central through bore with a diameter that fits closely over the lower module hub. In some embodiments, one or more of the guide bores of the upper module comprises an upper taper and a lower taper separated by a central channel, and further may include a reduced-diameter neck below the upper taper. The lower module in some embodiments includes a retaining member in one or more of the receptacles that is configured to apply a retention force on a follicular unit delivery tool placed therein to prevent the tool from falling out by gravity yet permit removal of the tool from the receptacle by a pick and place device. The retaining member may comprise an elastomeric ring, or a finger configured to compressibly retain the delivery tool. In other embodiments the retaining member may comprise a close fit between the delivery tool and the receptacle, or is may have an orifice sized slightly smaller than the delivery tool. The receptacles of the lower module, as well as corresponding guide bores of the upper module, may be arranged in various linear and non-linear patterns, including close-spaced patterns.

According to another aspect of the invention, a storage device is provided for holding a plurality of biological unit delivery tools each sized to carry a biological unit. The storage device includes a module having a plurality of receptacles each sized to receive a biological unit delivery tool, and a retaining member in each one of the receptacles that is configured to apply a retention force on the delivery tool when placed therein to prevent the tool from falling out by gravity, yet permit removal of the delivery tool from the receptacle upon application of a threshold force. The retaining member may have an orifice sized slightly smaller than the delivery tool. In one embodiment the retaining member comprises an elastomeric ring, such as O-ring. The biological unit delivery tools may be tools, such as needles or cannulas, for holding, for example, follicular units.

The storage device may further include a delivery tool formed as a tubular member, and the elastomeric ring defines an oval shape with a minor axis smaller than the tubular member for retention of the delivery tool, and a major axis larger than the tubular member. Consequently, a space exists between an inner edge of the elastomeric ring and the delivery tool along the major axis. Alternatively, the retaining member comprises a finger spaced from a wall, the finger and the wall defining a portion of the receptacle and being spaced apart slightly smaller than the delivery tool when placed therein, wherein the finger may flex to compressibly retain the delivery tool in the receptacle when placed therein. A still further option for the retaining member is a close fit between the delivery tool and the receptacle in conjunction with liquid in the receptacle that applies surface tension to the delivery tool when placed therein as the retention force.

The present invention also embodies a system for storing and delivering a follicular unit, comprising a storage device and a collet. The storage device is intended to hold a plurality of follicular unit delivery tools and comprises a lower module defining a plurality of receptacles sized to receive the follicular unit delivery tools. An upper module is configured to register with the lower module and has a plurality of guide bores, one for each receptacle in the lower module, wherein the upper module is separable from the lower module to expose upper ends of each of the delivery tools. The collet is configured to selectively pick up delivery tools from the lower module when present therein after the upper module has been separated and removed from the lower module.

The system may also include a follicular unit removal tool sized to carry at least one follicular unit and configured to be held by the collet. The present invention is particularly useful with an automated or robotic system that may manipulate the collet and removal tool so that the removal tool aligns with selected guide bores of the upper module, and a delivery mechanism expels the follicular unit from the removal tool held by the collet into the lower module receptacle. In one exemplary embodiment the delivery mechanism may comprise an elongated obturator that passes through the collet and removal tool, and in another exemplary embodiment the delivery mechanism may comprise a subsystem for creating a fluid pressure differential through the collet and removal tool. The system preferably includes a plurality of delivery tools, each held in the lower module receptacle and configured to accept follicular units from the removal tool.

The system described above may incorporate a delivery tool sized to carry a follicular unit, and a mechanism for expelling the follicular unit from the delivery tool after the delivery tool has been picked up from the lower module by the collet. For instance, the delivery mechanism may be an elongated obturator that passes through the collet and delivery tool. A robotic control system may be used to automatically displace the storage device and collet with respect to one another, and may include a camera for imaging a body surface, wherein the system is capable of automatically implanting hair follicles into the body surface. In one embodiment the delivery tools comprise needles.

The present invention also provides an automated process for acquiring and implanting a follicular unit. A follicular unit is urged into a guide bore of a storage device using a substantially automated process, the guide bore opening directly into a lumen of a delivery tool held in a receptacle of the storage device. The delivery tool having follicular unit therein is then removed from the storage device receptacle. Finally, the follicular unit is implanted into a body surface from the delivery tool using a substantially automated process. The process may further comprise urging the follicular unit from a harvesting tool into the storage device guide bore. The process desirably performs the steps of urging, removing, and implanting a plurality of times with a single storage device and multiple delivery tools.

According to still further aspect of the present invention, a system for storing and delivering a biological unit comprises a storage device for holding a plurality of biological unit delivery tools. The storage device includes a module defining a plurality of receptacles for receiving delivery tools, wherein the receptacles are closely-spaced a predetermined minimum distance apart from each other. A collet is arranged to selectively picking up delivery tools from the module and has a shaft with a radius greater than the predetermined minimum distance, the collet including a chuck on a distal end for holding delivery tools and recesses in the shaft surrounding the chuck enabling the collet to be positioned between delivery tools surrounding a target delivery tool so that the chuck can grab the target delivery tool. In one embodiment, the recesses are evenly distributed around the periphery of the collet shaft in the same pattern that a plurality of delivery tools in receptacles surrounds the target delivery tool. The receptacles for delivery tools may be arranged in various patterns, including linear and non-linear patterns.

Other and further objects and advantages of the invention will become apparent from the following detailed description when read in view of the accompanying figures.

BRIEF DESCRIPTION OF THE DRAWINGS

Features and advantages of the present invention will become appreciated as the same become better understood with reference to the specification, claims, and appended drawings wherein:

FIGS. 2A and 2B are exploded and assembled perspective views, respectively, of an exemplary biological unit storage device of the present invention;

FIG. 2C is an enlarged view of a portion of a tool retention embodiment of the biological unit storage device taken in the circle 2C of FIG. 2A;

FIG. 5 is a top plan view of an exemplary upper module of a biological unit storage device similar to that shown in FIG. 2A;

FIGS. 5A and 5B are radial and enlarged sectional views through the upper module of FIG. 5;

FIG. 6 is a top plan view of an exemplary lower module of a biological unit storage device similar to that shown in FIG. 2A;

FIG. 6A is a radial sectional view through the lower module of FIG. 6;

FIG. 7 is a side plan view of the lower module of FIG. 5;

FIGS. 8 and 8A are perspective and enlarged cut-away views of an alternative storage device showing an exemplary delivery tool retention feature;

FIG. 9 is a perspective, inverted exploded view of the alternative storage device of FIG. 8;

FIG. 10 is a top plan view of a portion of a lower module of FIG. 9 showing the delivery tool retention feature;

FIG. 11 is a close-up view of an exemplary implant or harvest tool held within a collet;

FIG. 12 is a perspective view of an alternative annular storage device of the present invention having a plurality of closely-packed receptacles for receiving tools or biological units;

FIG. 13 is a perspective view of a rectangular biological unit storage device of the present invention having a plurality of closely-packed receptacles for receiving tools or biological units, and also illustrating a collet accessing the receptacles; and FIG. 14 is a close-up view of a collet accessing one of a plurality of tools within the storage device of FIG. 13.

DETAILED DESCRIPTION OF THE PREFERRED EMBODIMENTS

Figure 1:
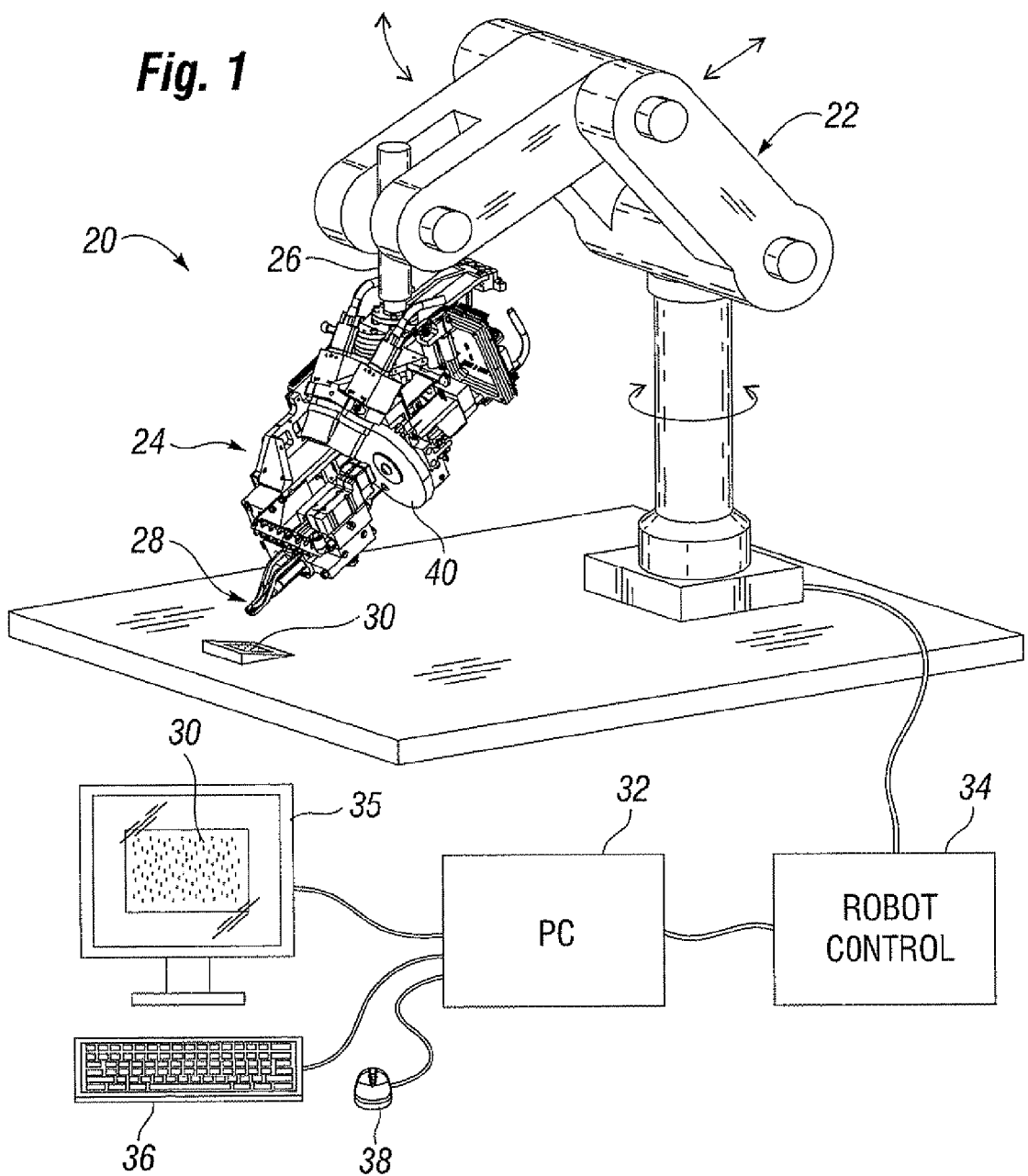
FIG. 1 is a schematic perspective view of an exemplary robotic biological unit harvesting and implanting system of the present invention.

In the following Detailed Description, reference is made to the accompanying drawings, in which are shown by way of illustration specific embodiments in which the invention may be practiced. In this regard, directional terms, such as "top," "bottom," "front," "back," "distal," "proximal," etc., are used with reference to the orientation of the Figure(s) being described. Because components or embodiments of the present invention can be positioned in a number of different orientations, the directional terminology is used for purposes of illustration and is in no way limiting. It is to be understood that other embodiments may be utilized and structural or logical changes may be made without departing from the scope of the present invention. The following Detailed Description, therefore, is not to be taken in a limiting sense, and the scope of the present invention is defined by the appended claims.

The adjective "automated" with reference to a system or process as a whole means that some part or all of a particular system or step in the process involves an autonomous mechanism or function; i.e., that mechanism or function does not require manual actuation. Ultimately, one or more steps in the procedure may be automated, or autonomous, with some parts requiring manual input. This definition encompasses an automated system that requires only an operator to depress an ON switch or schedule the operation, and also a system in which hand held tools are used but some mechanism of the system functions autonomously, i.e., without human input, to perform a function. Some of the automated processes described herein may also be robotically-assisted or computer/software/machine-instruction controlled. The devices and methods of the present invention are useful in manual procedures and systems, as well as in automated procedures and system, and they are especially useful in the robotically-assisted systems and procedures. In contrast, the adverb "automatically" when referred to use of a particular component of a system or a particular step in a process means that such step is accomplished autonomously, i.e., without real-time manual assistance.

The term "tool" as used in harvesting (or removal) tool with reference to hair transplantation or other procedure refers to any number of tools or end effectors that are capable of removing or harvesting FUs or other biological units from a body surface. Likewise, a "tool" as used in implanting tool or delivery tool with reference to hair transplantation or other procedure refers to any number of tools or end effectors that are capable of implanting/inserting FUs in a body surface, or otherwise delivering biological units to an end location. Likewise, some implant tools may serve dual or multiple purposes and also be capable of harvesting, removing, carrying, or handling FUs or other biological units. In this sense, a body surface can be attached to the body or be a flap of skin removed from the body. Such tools exist in many different forms and configurations. In some embodiments, the tool comprises a hollow tubular shaft having an angled tip leading to a sharp point. The distal end of removal tools (for example, punches, coring devices, cutting and/or trimming devices, needles), are typically sharpened, to cut and extract the tissue (e.g., hair follicle). Implanting tools may also be sharpened so as to perform puncture and delivery of the FU in one operation. However, the puncture may be formed by another tool, with the implanting tool being relatively blunt and used just for delivery of the FU. Or, the delivery tool may be adapted simply for holding a biological unit until such time it is transferred to an intended location; for example, biopsies may be delivered to test tubes. It also should be noted that the removal and delivery tools could be the same or different instrument, depending on the procedure and objects to be removed (e.g., harvested) or delivered (e.g., implanted). These general principles will be described herein with respect to the specific environments of harvesting and implanting hair follicles, though the invention should not be considered to be so limited.

The present invention utilizes a storage device into which delivery tools holding biological units are placed. The storage device includes receptacles for receiving the delivery tools, and may be immediately utilized to present the biological units for delivery to an end location, or may be preserved and stored for later use. The storage device may be alternately referenced herein as a cartridge or storage cartridge. It should be understood that the exemplary storage devices (e.g., a cartridge for hair follicles) of the present invention are especially suited for use with a robotic system or computer-controlled system. However, certain principles of the storage devices also provide improvements that could be used with manual, other automated or partially automated systems and devices.

"Biological units" includes discrete units used in cosmetic and dermatological procedures, for example, various tissue, including that extracted for biopsies or grafting, fat units, skin units, etc. One example of biological units particularly useful with the present invention is hair grafts, or follicles, or "follicular unit(s)." The term follicular units (or FUs) will be used herein simply as an example for purposes of describing some embodiments of the present invention with the understanding that it represents more broadly biological units.

The present invention discloses an exemplary system and storage device useful for harvesting and implanting follicular units. The present invention is particularly useful in robotic hair transplantation, to provide an automated system and a storage device for harvesting and implanting follicular units (FUs). An entire robotic system will be described first, and it should be understood that the robotic principles and mechanism that are described facilitate rapid and efficient hair transplant operations, although particular structures described herein may be useful with manual or semi-automated systems.

FIG. 1 is a schematic perspective view of an exemplary robotic biological unit harvesting and implant system 20 according to one aspect of the present invention. The system 20 includes a robotic arm 22 having a head assembly 24 mounted for rotation on a down tube 26 of the robotic arm. Various arrows are shown to illustrate the movement capabilities of the system 20. Furthermore, as will be seen below, motors and other such movement devices incorporated in the head assembly 24 enable fine movements of an operating tip 28 in multiple directions.

The operating tip 28 is shown positioned over a body surface 30, in this case a strip of tissue having hair follicles thereon. A personal computer 32 acting, for example, through a robotic control 34 controls the various movement devices of the robotic arm 22 and head assembly 24. An operator monitors conditions and provides instructions through a monitor 35, keyboard 36, and mouse 38. A magnified image of the body surface 30 can be seen on the monitor 35 generated by video system cameras mounted on the head assembly to provide depth perspective.

The present invention primarily pertains to an improved storage device for biological unit delivery tools, and in particular follicular unit implant tools. An exemplary embodiment of the system 20 manipulates the operating tip 28 into position to harvest or remove biological units such as follicular units from the body surface 30. In the illustrated embodiment, the body surface 30 comprises a strip of skin that has been removed from a subject, although the system 20 could also be utilized to remove biological units directly from the subject. Although not shown, the operating tip 28 incorporates a harvesting or removal tool which contacts the body surface 30 and physically captures the biological unit. For instance, follicular units may be removed by a hollow tubular tool, such as a coring needle.

Subsequently, the system 20 transfers the removed biological unit to a storage device schematically shown at 40, as will be explained in greater detail below. The storage device 40 may be immediately utilized in the system 20 to provide biological units for re-implantation or other use. Alternatively, the storage device 40, once full, is removed from the system 20 for safekeeping and later use in re-implantation or other desired procedure, analysis or testing.

Figure 1A:
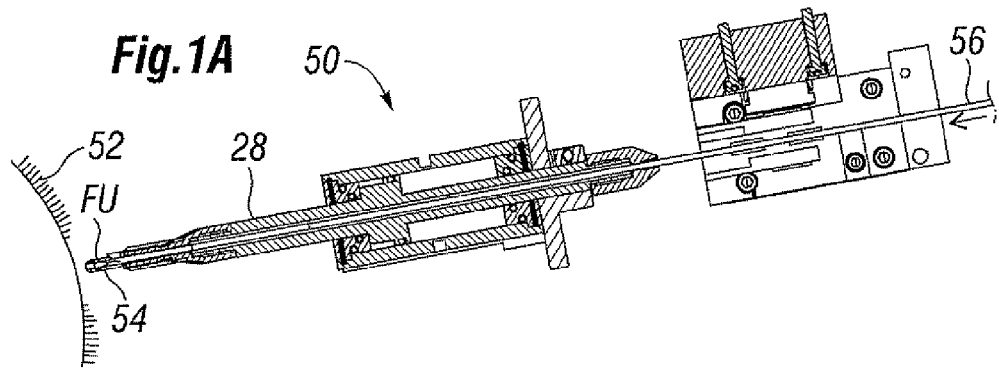
FIG. 1A is a longitudinal sectional view through an exemplary subsystem for use in the system of FIG. 1 for implanting hair follicles into areas of need on a person's scalp.

FIG. 1A is one embodiment of a re-implantation subsystem 50 that could form part of the system 20 shown in FIG. 1. The particular implant subsystem 50 shown facilitates an automated or semi-automated process for implanting hair follicles into areas of need on a body surface 52 (e.g., a person's scalp). The subsystem 50 includes the operating tip 28 holding a delivery tool 54 within which is carried a follicular unit (FU). In this embodiment, the subsystem 50 further includes an elongated obturator 56 that travels through the operating tip 28 and through the delivery tool 54. The operation proceeds by inserting the delivery tool 54 and using the tool itself to form the puncture (or inserting the tool into a pre-formed puncture in the body surface 52) and then pushing the FU from the tool using the obturator 56. Typically, the operating tip 28 and delivery tool 54 are retracted while holding the obturator 56 in place which causes the FU to remain in the puncture.

Once again, the same or a similar mechanism could be utilized to deliver other biological units, such as biopsy samples, to end locations such as test tubes. The illustrated hair implant subsystem 50 is representative of other such applications of the present invention.

The present invention utilizes storage devices for multiple delivery tools 54. In the embodiment illustrated in FIG. 1A; the delivery tool 54 comprises an implant needle for an FU. Multiple implant needles are stored and picked up by the operating tip 28 one-by-one for use in implanting the FUs. It should be appreciated that various exemplary embodiments of the storage devices described herein are designed and sized to store delivery/implant tools; however, they could be manufactured and sold separately from the delivery/implant tools. In fact, the tools could be made and/or sold by third parties. Similarly, if the tools and the storage devices are used in the robotic systems, each of the system itself storage devices, and delivery/implant tools could be sold separately by various independent parties; alternatively, any combination of these components could be sold together as a kit.

One exemplary embodiment of a storage device of the present invention is shown at 60 in FIGS. 2A and 2B. The storage device 60 comprises an upper module 62 that registers with a lower module 64. In the illustrated embodiment, both the upper and lower modules 62, 64 are generally annular disc-like in shape having circular peripheries and central throughbores. A plurality of guide bores 66 extend vertically entirely through the height dimension of the upper module 62 near its outer periphery. A plurality of vertical receptacles 68 within the lower modules 64 receive and retain delivery tools 70. In the illustrated embodiment the delivery tools 70 comprise follicular unit implant tools that are small tubes including an angled tip leading to a sharp point (i.e., small needles). As explained above, such delivery tools 70 are separate items from the storage device itself, and they do not have to be sold or packaged with the storage device.

As mentioned above, the term "biological unit" refers to discrete units used in cosmetic and dermatological procedures, for example, hair grafts, or follicles. The size of the biological unit, and therefore the delivery tool that carries it, is variable, and consequently the size of the receptacles 68 also varies depending on the particular delivery tool. One particular embodiment described herein is the aforementioned follicular unit implant tool that carried a follicular unit. A single hair follicle is known to have a width of between about 50 microns ("μm") and 100 μm, with an average of about 75 μm. A follicular unit (FU) may comprise a single hair follicle, or multiple hair follicles, for example, 2 to 5 hair follicles. Therefore, the width or caliber of the multiple hair FU is several times larger than a single hair follicle FU based on the number of hairs in the FU. The corresponding implant tool therefore has a lumen with a diameter sized to receive single or multiple FUs, and the outer diameter of the tool that cooperates with the receptacle 68 is slightly larger because of the wall thickness of the tool.

Figure 3:
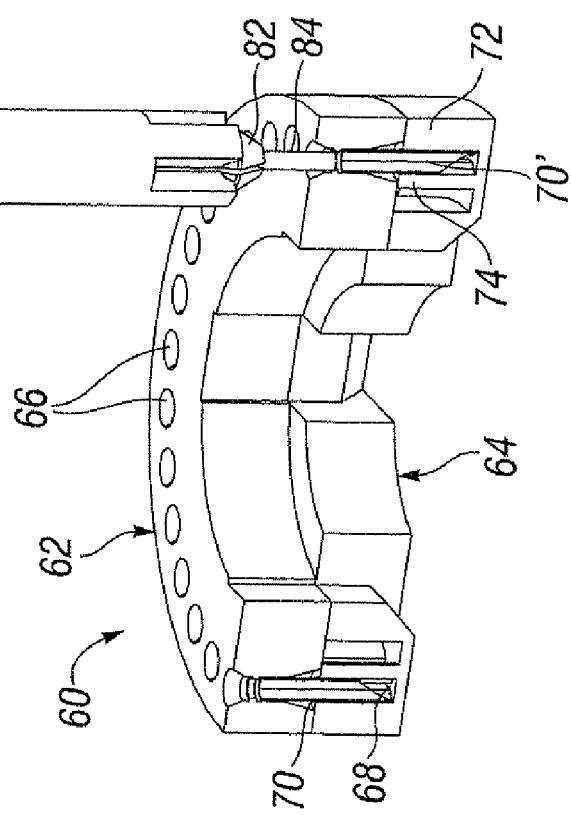
FIG. 3 is a perspective cut-away view through the exemplary biological unit storage device of FIG. 2A showing robotic delivery of a biological unit from a harvest tool into a carrying tool within the storage device.

In some embodiments, the receptacles 68 are "dead-end" wells in that they are closed at their lower ends and, as seen in FIG. 2A, are suitable for holding liquid, such as saline to keep, for example, FU in the delivery needles moist, as described in more detail in reference to FIG. 3. However, while the bottom of the lower module of the storage device 60 may be closed off, all or some of the receptacles 68 may be interconnected with each other, for example, at their bottoms to help transport hydrating/lubricating liquid or gas between the receptacles 68, if desired. Alternatively, in some embodiments, for example, where there is no need to keep the biological unit moist, or where the storage device 60 is used to store, for example, harvesting tools that do not contain the follicular unit yet, the receptacles 68 and/or the bottom of the lower module/receptacles 68 do not have to be completely closed off. In those embodiments where receptacles 68 have holes through the bottom of the lower module of the storage device, it is desirable to employ some retention feature or member that would prevent the delivery device to fall out from the storage device. Various non-limiting examples of such retention features are described herein. The depth of the receptacles 68 is less than the height of the tools 70 such that the upper ends of the tools project upward from the lower module 64. Each of the guide bores 66 aligns with one of the receptacles 68 such that the upper ends of the delivery tools 70 extend into the guide bores when the upper module 62 couples with the lower module 64.

Each receptacle 68 retains a tool 70 therein with a retention force that helps a pick and place tool, for example a collet, cleanly release the tool. That is, sometimes the collet does not fully release the tool 70 when placing it in the receptacles 68. As will be more clear below, the retention force holding the tools 70 permits a pick and place collet to insert a tool into a receptacle 68 such that it is retained therein and will not easily pull free. In a preferred embodiment, the retention force on each tool 70 is less than the force that holds the tool in the CLOSED collet, so that the collet can remove the tool when desired. However to ensure the tool 70 is positively released from the collet, the tool retention force in each receptacle 68 is greater than any frictional force that acts on the tool by the OPEN collet. In an exemplary embodiment, the tool retention force of each receptacle is equal to or less than about 1 lb (4.45 N).

In the exemplary embodiment of FIG. 2A, as best seen in FIG. 2C, each receptacle 68 may comprise a partial cylindrical indent in an outer wall 72 of the lower module 64 in conjunction with a retention finger 74. These two components of the receptacle 68 can also be seen in the sectional view of FIG. 3. The retention fingers 74 extend upward from a base surface of the lower module 64 in a cantilevered fashion. Each retention finger 74 has a partial cylindrical indent opposed to an indent in the outer wall 72, so that together a partial cylinder is defined having a diameter that is slightly smaller than the diameter of each of the delivery tools 70. The upper and lower modules 62, 64 are desirably molded plastic parts, and the cantilevered arrangement of the fingers 74 enables them to flex a slight amount when the delivery tools 70 are positioned in the receptacle 68. The slight compressive retention force applied by each finger 74 against the delivery tool 70 and reaction force of the outer wall 72 is sufficient to retain the delivery tools in the lower module 64, even if the pick and place collet does not fully release the tool when OPEN (that is, some frictional contact may exist between the collet and tool). At same time, however, each delivery tool 70 may be easily removed by firmly pulling it upward from the corresponding receptacle 68, because the tool retention force is less than the upward force of the CLOSED collet (the lower module will typically be firmly engaged by a clamp or seat of some sort in the system 20).

The assembly of the upper and lower modules 62, 64, seen in FIG. 2B, presents a storage device 60 that can be easily rotated by engaging the central through bores with a keyed shaft to present selected guide bores 66 to a pick and place collet 80 (FIGS. 3 and 4) that can deposit biological units therein. Likewise, with the upper module 62 removed, the lower module 64 may be rotated to present selected delivery tools 70 to a pick and place collet used to move the delivery tool to a desired location (e.g., the scalp of the subject).

With reference to FIG. 3, the assembled storage device 60 is shown in vertical cut-away with delivery tools 70 resting in the receptacles 68 of the lower unit 64. As mentioned above, the tools 70 project upward from the lower unit 64 and into the guide bores 66 of the upper unit 62. A pick and place tool such as a collet 80 carries a chuck 82 on its distal end which in turn holds a removal tool 84 (an examplary pick and place tool is seen in greater detail in FIG. 11). The removal tool 84 is shown extending slightly within one of the guide bores 66 in line with one of the delivery tools 70. Although not shown, the removal tool 84 encloses a biological unit which will be deposited within the delivery tool 70. The mechanism for depositing the biological unit into the delivery tool 70 is not critical, and could be, for example, a solid obturator or pressurized fluid or air. Because of the dead-end nature of the examplary receptacles 68 in the lower module 64, a small amount of lubricating/hydrating fluid may be provided in the receptacles to maintain the biological unit hydrated. For example, saline may be provided in the receptacles 68 to hydrate FUs. In one embodiment, the system includes a subsystem for creating a fluid pressure differential through the removal tool 84 such that pressurized saline may be used to expel the biological unit from the removal tool, which simultaneously deposits a requisite amount of saline into the receptacles 68. In some embodiments, as mentioned before, the receptacles 68 may be open and interconnected at the bottom to transport saline across, while the lower module 64 as a whole is enclosed.

Figure 4:
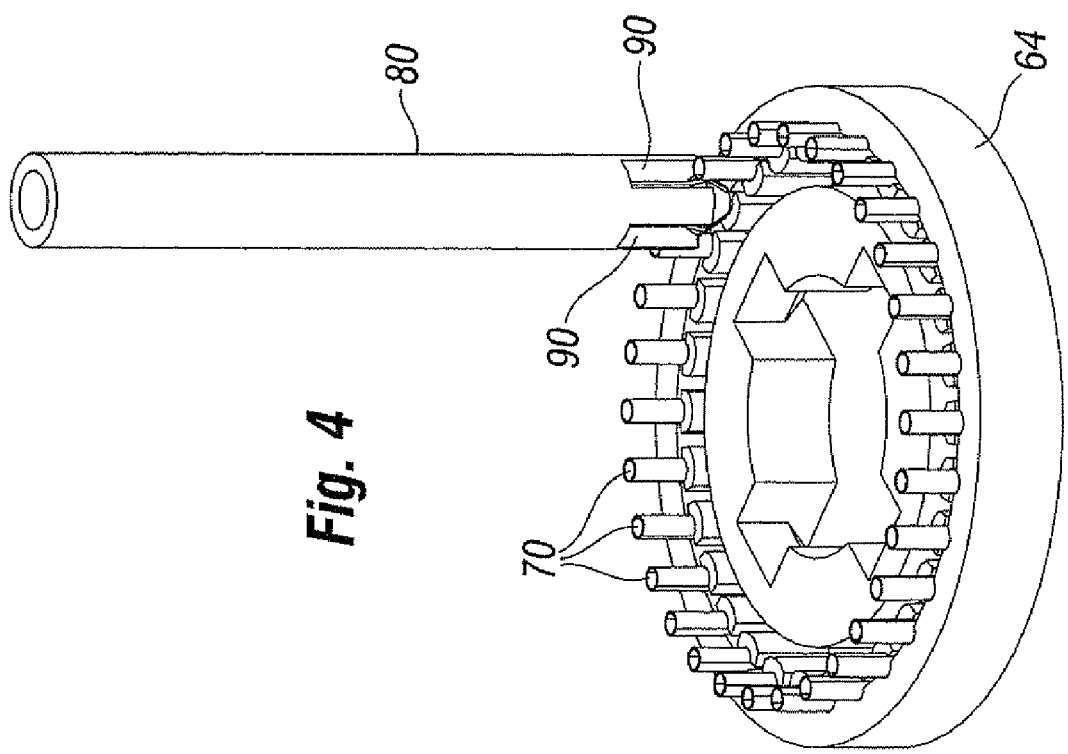
FIG. 4 is a perspective view of the lower module of the biological unit storage device with the upper module removed and a collet manipulating one of the delivery tools within the storage device.

FIG. 4 illustrates the lower module 64 by itself with the upper module 62 removed. Each of the receptacles 68 retains therein a delivery tool 70, whose upper ends project above a top surface of the lower module 64. A pick and place tool such as the collet 80 is shown engaging one of the tools 70. The reader will understand that the pick and place tool may take a number of forms, including that shown in FIG. 3 with the chuck 82, but with the removal tool 84 omitted. The chuck 82 may be actuated to open and close and alternately grab and release the delivery tools 70. In this way, the collet 80 may be manipulated manually, semi-automatically, or completely automatically (including robotically) to pick up selected tools 70 and use them in a delivery procedure, such as a follicular unit implant procedure.

According to another aspect of the present invention, the lower end of the collet 80 features several recesses 90 that enable the receptacles 68 to be more closely spaced than otherwise would be possible. More particularly, the collet 80 typically includes a shaft having a first radius that is greater than a predetermined minimum spacing between the receptacles 68. Without the recesses 90, the shaft of the collet 80 would not be able to descend in between the tools to pick up a selected one. The recesses 90 are elongated and opposed across the collet so that they align with the two tools on either side of a target tool. This aspect of the present invention means that for a given number of tools stored in the storage device, the size of the storage may be reduced from a system without the recesses 90 in the collet 80. Viewed another way, more tools may be stored in a given storage device than if the collet were not recessed.

FIGS. 5-7 illustrate in detail alternative upper and lower modules for an exemplary biological unit storage device of the present invention. Details of an exemplary upper module 100 can be seen in FIGS. 5, 5A, and 5B, while an exemplary lower module 102 is depicted in FIGS. 6, 6A, and 7. In contrast to the earlier-described embodiment, the modules 100, 102 are not continuous around the periphery, instead are interrupted by recesses especially useful for robotic manipulation. Both upper and lower modules 100, 102 may be machined, but desirably are molded of a relatively hard polymer such as Lexan, a polycarbonate resin thermoplastic.

The upper module 100 seen in FIG. 5 is generally disc-shaped with an upper face 104 parallel to a lower face 106. The module 100 may include, as seen in FIG. 5, a circular outer edge 108 around approximately 75% of its periphery, interrupted by a first, generally convex-concentric cutout 110, and a second smaller radius concave cutout 112. The module 100 defines a plurality of guide bores 114 generally evenly circumferentially spaced and close to the outer edge 108 in the arc outside the cutouts 110, 112. In one embodiment, there are 25 guide bores 114 spaced apart in an arc S between 10-11° from each other. The illustrated upper module 100 has an outer diameter of 2.5 inches, and a central bore of 1.265 inches. The guide bores 114 lie along a circle having a diameter of about 2.25 inches. The exemplary thickness across the upper and lower faces 104, 106 is 0.344 inches.

FIGS. 5A and 5B illustrate details of the shape of each of the exemplary guide bores 114. The bores 114 include an upper taper 120, a lower taper 122, a central channel 124, and a circular neck 126 separating the upper taper and central channel. The shape of the guide bores 114 is similar to the shape of the guide bores 66 in the earlier-described embodiment, and as seen in FIG. 3. As such, dimensions for the modules 100, 102 will be described relative to the cooperating components of the overall system as described above. The diameter D of the central channel 124 is sized slightly larger than the outer diameter of each of the delivery tools 70, but the smaller diameter d of the neck 126 is less than the diameter of the delivery tools. For instance, d=0.055 inches and D=0.067 inches. When the upper module 100 (or module 62) registers with the lower module 102 (or module 64), the neck 126 retains the delivery tools 70 within the lower module receptacles.

Any of the examplary guide bores 114 may include the upper and lower tapers 120, 122, to facilitate interaction with the removal and delivery tools of the system. In particular, as seen in the embodiment of FIG. 3, the removal tool 84 inserts into the upper taper before depositing a biological unit in the delivery tools 70. The upper taper 120 therefore accommodates any slight misalignment of the cooperating parts and centers the removal tool 84 over the delivery tool 70. Likewise, the lower taper 122 facilitates registry of the upper module 100 with the lower module 102 by accommodating any misalignment or tolerances between the upstanding tools 70 and the lower ends of the guide bores 114. The upper taper 120 has an included angle $\alpha$, while the lower taper 122 has an included angle $\beta$. Preferably, $\alpha$ and $\beta$ both equal 30°.

The examplary lower module 102 seen in FIGS. 6-7 comprises a central raised hub 130 surrounded by a well 132, which in turn is circumscribed by an outer wall 134. The central hub 130 has an outer diameter that fits closely within the inner diameter of the central bore of the upper module 100, so that the two parts may be easily registered. The height of the hub 130 above the outer wall 134 is desirably the same as the thickness of the upper module 100 (0.344 inches) so that the two parts mated describe a cylinder. Likewise, the lower module 102 includes a concave cutout 140 that matches up with the concave cutout 112 in the upper module 100 (the shown shapes of the cutouts 112 and 140 are examplary only). The two cutouts 112, 140 provide a recessed for axial movement of the collet 80 (not shown). By rotating the storage device different guide bores 114 (and receptacles 142 described below) may be aligned on the axis of the collet 80.

A plurality of receptacles 142 may be evenly spaced in the outer wall 134, corresponding to the number of guide bores 114 in the upper module 100, as described above. The examplary shape of the receptacles 142 is seen on the right side of FIG. 6A, and preferably includes an entry taper 144 and a constant diameter well. The diameter of each receptacle 142 is desirably closely matched with the outer diameter of the delivery tools 70, and the retention feature in this embodiment comprises surface tension of a lubricating liquid. That is, the clearance between the tools and the receptacles are so close that lubricating liquid provides enough surface tension attraction force to retain the tools in place if a pick and place collet does not cleanly release the tool.

According to a further aspect of the present invention, FIGS. 8-10 illustrated an alternative lower module 150 showing an exemplary delivery tool retention feature. The lower module 150 is shaped similarly to the module 102 of FIGS. 6-7, though instead of being a unitary component is formed of a main body 152 and a horseshoe-shaped lower brace 154. The brace 154 closely fits over an arcuate ledge 156 on the underside of the main body 152 and covers a plurality of oval-shaped wells 158. A plurality of bolts (not shown) secures the brace 154 onto the ledge 156. Alternatively, the brace 154 can be secured onto the ledge 156 by various non-limiting mechanical and non-mechanical attachments, for example, it could be press-fit, or glued.

A series of peripheral receptacles are defined by through bores 160 in the main body 152 aligned with bores 161 in the brace 154 (see FIG. 8A). As with other described embodiments, bores 161 may be dead-end bores to hold saline or other hydrating fluid/gas, or they may lead to a dead-end bottom portion of the brace 154 but be interconnected with each other to transport such hydrating fluid/gas, or they may be through bores if holding liquid/gas is not needed. In between each of the bores 160, 161 is positioned an exemplary elastomeric ring, such as O-ring 162, captured in the well 158 between the main body 152 and lower brace 154. By virtue of the constraint imposed by the oval-shaped well 158, the O-ring 162 deforms to have a minor inner diameter smaller than the outer diameter of a delivery tool 164, and a major inner diameter larger than the tool diameter. As with other retention features described above, the contact between the tool 164 and O-ring 162 along its minor axis creates a frictional holding force on the tool 164 and helps a pick and place collet cleanly release the tool. The retaining member may take shapes and forms other than the exemplary O-ring 162, as long as is it is configured to apply a retention force on the tool when the tool is placed in the receptacle to prevent the tool from falling out by gravity yet permit removal of the tool from the receptacle upon application of a threshold force.

As seen in FIG. 10, a small space 166 between the O-ring 162 aperture and the tool 164 helps prevent nicking of the O-ring by a sharp point 168 of the tool. The space 166 is created by offset placement of the well 158 relative to the bores 160, 161. The tool 164 should therefore be oriented with the sharp point 168 toward the space 166, in this case radially outward.

FIG. 11 is a close-up view of the distal end of the collet 80 described above. The chuck 82 may be segmented into four quadrants for easy gripping and release of the delivery tool 70 (or removal tool 84, for a FU depositing operation). As is known, axial displacement of the chuck 82 may be used to cause its four teeth to open and close. The side recesses 90 are also shown, and comprise elongated partial cylindrical cutouts.

FIG. 12 schematically illustrates an alternative upper or lower module 180. The module has an annular disc shape, as described in the previous embodiments, though the apertures 182 visible on the upper surface, representing either the guide bores of the upper module or receptacles of the lower module, are not linearly circumferentially spaced. Instead, the apertures 182 are closely-packed in a two-dimensional array so as to fit more densely within the surface area of the module 180, and therefore, this non-linear arrangement allows the storage device to hold more tools. In addition to increasing capacity of the storage device by a non-linear arrangement of the location of the receptacles for holding tools, as described above, the recesses 90 in the shaft of the collet 80 permit the collet to access closely-spaced apertures 182 by interlacing between tools. For instance, an annular module 180 having an outer diameter of less than 1.5 inches may be able to hold about 100 biological units within tools held in the apertures 182. Furthermore, robotic pick and place travel distance and time is reduced because of the smaller distances between apertures 182. To summarize, either of these described features alone or in combination provides for the increased capacity of the storage device.

FIG. 13 and the enlarged view of FIG. 14 illustrate a rectangular lower module 190 having a plurality of closely-packed receptacles 192 in a two-dimensional array holding delivery tools 194. A collet 80 is shown descending down below the level of the projecting tools 194, and the enlarged view of FIG. 14 shows two adjacent tools 194 within the outer diameter of the shaft of the collet 80, in the recesses 90. The recesses 90 are desirably evenly distributed around the periphery of the collet 80 in the same pattern that a plurality of delivery tools 194 in receptacles surrounds the target delivery tool. For instance, each tool 194 is surrounded by four others, and likewise there are four evenly spaced recesses on the collet 90. Because of this accommodation, the receptacles 192 may be spaced apart closer than the radius of the collet 80, and more biological units can be stored in a given storage space. For instance, a rectangular module 190 sized 3×5 inches may include about 1000 receptacles 192.

In use, the present invention in any of the forms described above is capable of automatically acquiring, storing and implanting a follicular unit, or more generally for storing and delivering a biological unit. In the exemplary embodiment involving follicular units, the process includes urging a follicular unit into a guide bore of the storage device using a substantially automated process. That is, for instance, a robotic harvesting tool may acquire a follicular unit and deposit it into the guide bore. The guide bore opens directly into a lumen of a delivery tool held in a receptacle of the storage device, and thus the follicular unit is rapidly deposited into the delivery tool. Typically, the delivery tool is a follicular unit implant needle. The same single harvesting tool may be used to deposit multiple follicular units in multiple delivery tools.

The process then involves removing the delivery tool having follicular unit therein from the storage device receptacle, and implanting the follicular unit into a body surface from the delivery tool using a substantially automated process. In other words, a pick and place collet grabs each delivery tool (implant needle) and uses it to implant the follicular unit. After use, the implant needle may be discarded or placed back into the receptacle from which it came. In a desired procedure, the steps of urging, removing, and implanting are repeated a plurality of times with a single storage device and multiple delivery tools. This automated process greatly speeds up and improves the process of hair transplantation as compared with a purely manual procedure.

The foregoing illustrated and described embodiments of the invention are susceptible to various modifications and alternative forms, and it should be understood that the invention generally, as well as the specific embodiments described herein, are not limited to the particular forms or methods disclosed, and that many other embodiments are possible within the spirit and the scope of the present invention. Moreover, although individual features of one embodiment of the invention may be discussed herein or shown in the drawings of the one embodiment and not in other embodiments, it should be apparent that individual features of one embodiment may be combined with one or more features of another embodiment or features from a plurality of embodiments.

While the invention has been described in its preferred embodiments, it is to be understood that the words which have been used are words of description and not of limitation. Therefore, changes may be made within the appended claims without departing from the true scope of the invention.

What is claimed is:

1. A system for storing and delivering a follicular unit, comprising:
    a storage device for holding a plurality of follicular unit delivery tools comprising a lower module defining a plurality of receptacles each sized to receive a follicular unit delivery tools, and an upper module configured to register with the lower module and having a plurality of guide bores, one for each receptacle in the lower module, wherein the upper module is separable from the lower module to expose upper ends of each of the delivery tools;
    a collet configured to selectively pick up the delivery tool from the lower module when present therein after the upper module has been separated and removed from the lower module; and
    a mechanism comprising an elongated obturator configured to pass through the collet and the delivery tool and to expel the follicular unit from the delivery tool after the delivery tool has been picked up from the lower module by the collet.

2. The system of claim 1, further comprising:
    a follicular unit removal tool sized to carry at least one follicular unit and configured to be held by the collet; and
    an automated system for manipulating the collet and the removal tool so that the removal tool aligns with selected guide bores of the upper module.

3. The system of claim 2, wherein the elongated obturator is configured to pass through the removal tool.

4. The system of claim 2, therein the mechanism comprises a subsystem for creating a fluid pressure differential through the collet and the removal tool.

5. The system of claim 2, further including a plurality of delivery tools, each held in the lower module receptacle and configured to accept follicular units from the removal tool.

6. The system of claim 1, further including a robotic control system for automatically displacing the storage device and the collet with respect to one another.

7. The system of claim 6, further comprising delivery tools each configured to hold a follicular unit, and the robotic control system includes a camera for imaging a body surface, and the system is capable of automatically implanting hair follicles into the body surface.

8. The system of claim 7, wherein the delivery tools comprise needles.

9. The system of claim 1, wherein each receptacle in the lower module has an upper opening and a cross-sectional dimension suitable for closely containing the follicular unit delivery tool.

10. The system of claim 1, wherein the plurality of follicular unit delivery tools is a plurality of follicular unit implant tools, and wherein the lower module is closed off at its lower end and one or more of the plurality of receptacles is configured to retain a liquid or gas.

11. The system of claim 1, wherein one or more of the plurality of receptacles is interconnected and configured to retain or transport, or both retain and transport, liquid or gas.

12. The system of claim 1, wherein the lower module comprises a central upstanding hub having an outer diameter, and the upper module has a central through bore with a diameter that fits closely over the lower module hub.

13. The system of claim 1, wherein one or more of the plurality of guide bores of the upper module comprises an upper taper and a lower taper separated by a central channel.

14. The system of claim 1, wherein the lower module further includes a retaining member in one or more of the plurality of receptacles that is configured to apply a retention force on the follicular unit delivery tool placed therein to prevent the tool from falling out by gravity yet permit removal of the tool from the receptacle.

15. The system of claim 1, wherein the plurality of receptacles are arranged in a closely-spaced non-linear pattern.

* * * * *